United States Patent
Wadman et al.

(10) Patent No.: US 9,963,437 B2
(45) Date of Patent: May 8, 2018

(54) PROCESS FOR THE PRODUCTION OF FURAN AND ITS DERIVATIVES

(71) Applicant: SHELL OIL COMPANY, Houston, TX (US)

(72) Inventors: Sipke Hidde Wadman, Amsterdam (NL); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days. days.

(21) Appl. No.: 15/129,856

(22) PCT Filed: Mar. 26, 2015

(86) PCT No.: PCT/EP2015/056628
§ 371 (c)(1),
(2) Date: Sep. 28, 2016

(87) PCT Pub. No.: WO2015/150238
PCT Pub. Date: Oct. 8, 2015

(65) Prior Publication Data
US 2017/0152237 A1    Jun. 1, 2017

(30) Foreign Application Priority Data
Mar. 31, 2014    (EP) ..................................... 14162654

(51) Int. Cl.
*C07D 307/02* (2006.01)
*C07D 307/36* (2006.01)

(52) U.S. Cl.
CPC .................... *C07D 307/36* (2013.01)

(58) Field of Classification Search
CPC ...................................................... C07D 307/36
USPC .......................................................... 549/505
See application file for complete search history.

(56) References Cited

U.S. PATENT DOCUMENTS 5,905,159 A  *  5/1999  Fischer .................. C07C 29/132
                                                        549/429

FOREIGN PATENT DOCUMENTS

| CN | 101874026 A | 10/2010 |
|----|-------------|---------|
| CN | 101967133 A | 2/2011 |
| CN | 102000569 A | 4/2011 |
| EP | 96913 | 12/1983 |
| JP | 2013158594 | * 8/2013 |
| WO | 2002022593 | 9/2001 |
| WO | 2012041990 | 4/2012 |

OTHER PUBLICATIONS

Dunlop, A.P. et al.: The Furans, "Furan and its Homologs", pp. 31-32, 1953.

(Continued)

*Primary Examiner* — Taylor V Oh

(57) ABSTRACT

The present invention provides a process for the treatment of a liquid first furan stream comprising furan and carbon monoxide, said process comprising the steps of: i) contacting said first furan stream with a CO-lean first gaseous stream; and ii) stripping at least a portion of the carbon monoxide in the first furan stream into the first gaseous stream to produce a second furan stream comprising less carbon monoxide than the first furan stream and a CO-enriched second gaseous stream.

13 Claims, 3 Drawing Sheets

(56) References Cited

OTHER PUBLICATIONS

Hoydonckx, H.E., et al. Ullmann's, "Furfural and Derivatives", vol. 16, pp. 285-313, 2012.
Lange, J-P., et al.: Chemsuschem 2012, "Furfural—A Promising Platform for Lignocellulosic Biofuels", DOI 10.1002/esse201100648, 5, pp. 150-166.
Watson, James M.: Ind. Eng. Chem. Prod. Res. Develop."Butane-1,4-diol from Hydrolytic Reduction of Furan", vol. 12, No. 4, 1973, pp. 310-311.
Zeitsch, Karl J.: Sugar Series, 13, "The chemistry and technology of furfural and its many by-products", Elsevier, 2000, pp. 150-155.
International Search Report dated Apr. 23, 2015 of PCT/EP2015/056628 filed Mar. 26, 2015.

* cited by examiner

PROCESS FOR THE PRODUCTION OF FURAN AND ITS DERIVATIVES

PRIORITY CLAIM

The present application is a National Stage (§ 371) application of PCT/EP2015/056628, filed 26 Mar. 2015, which claims priority from European patent Application 14162654.9 filed 31 Mar. 2014, each of which are hereby incorporated by reference in their entirety.

FIELD OF THE INVENTION

The present invention relates to a process for the production of furan and its derivatives.

BACKGROUND OF THE INVENTION

Furan and its derivatives are useful precursors for industrial chemicals in the area of, for example, pharmaceuticals, herbicides and polymers. Furan can readily be converted into tetrahydrofuran (THF) and 1,4-butanediol (1,4-BDO), which are valuable chemicals used industrially as solvents and in the production of elastic fibres such as elastane/spandex, polybutyrate terephthalate and derivatives of gamma butyrolactone.

These chemicals are usually produced industrially via a number of routes from petrochemical feedstocks, obtainable from fossil fuels. One industrial route for the production of 1,4-BDO requires the reaction of acetylene with two equivalents of formaldehyde followed by hydrogenation of the resultant 1,4-butynediol to form 1,4-butanediol. In an alternative process, propylene oxide is converted to allyl alcohol. The allyl alcohol is then hydroformylated to form 4-hydroxybutyraldehyde, which may be hydrogenated to form 1,4-butanediol. Other traditional routes use butadiene, allyl acetate or succinic acid as starting materials.

1,4-butanediol may also be produced as a side-product in a method for making tetrahydrofuran (THF) by oxidizing n-butane to crude maleic anhydride followed by catalytic hydrogenation.

In recent years, increased efforts have focused on producing chemicals, including furan and its derivatives such as 1,4-BDO and THF, from renewable feedstocks, such as sugar-based materials.

A method for obtaining furan from non-fossil fuel based sources involves the decarbonylation of furfural. Examples of reaction processes for achieving this and the subsequent conversion of the furan into its derivatives can be found in Hoydonck, H. E., Van Rhijn, W. M., Van Rhijn, W., De Vos, D. E. & Jacobs, P. A. (2012) Furfural and Derivatives, in Ulmann's Encyclopedia of Industrial Chemistry (volume 16, pp 285-313), Wiley-VCH Verlag GmBH & Co. KGaA, Weinheim; Dunlop, A. P. and Peters, F. N., in The Furans Reinhold Publ. Co, 1953; K. J. Zeitsch, in "The Chemistry and Technology of Furfural and its Many By-products" Sugar Series 13, Elsevier, 2000; Lange, J-P, van der Heide, E, van Buijtenen, J., and Price, R.; Furfural-A Promising Platform for Lignocellulosic Biofuels; ChemSusChem 2012, 5, 150-166 and Watson, J. M., Ind. Eng. Chem. Prod. Res. Develop., 1973, 12(4), 310. Furfural may be obtained from hemicellulose via acid hydrolysis in the liquid phase as well as in the gas phase as described in WO 2002/22593 and WO 2012/041990.

The product stream from a reaction process including the decarbonylation of furfural will contain furan, carbon monoxide, hydrogen and other by-products. Carbon monoxide often acts as a poison to catalysts used in subsequent reactions to convert furan into THF and 1,4-BDO and should be removed from the product stream. This may be carried out by condensation of the furan after considerable compression and cooling of the stream comprising furan, CO and $H_2$, for example to greater than 1.5 MPa and less than 20° C. However, due to the low boiling point of furan (31.3° C.), it is difficult to remove carbon monoxide from this mixture by distillation without substantial losses of furan.

It would, therefore, be advantageous to provide a method for the production of furan from furfural in which the furan may be separated from undesirable by-products, such as carbon monoxide, made in its production without significant losses of useful materials.

SUMMARY OF THE INVENTION

Accordingly, the present invention provides a process for the treatment of a liquid first furan stream comprising furan and carbon monoxide, said process comprising the steps of:
i) contacting said first furan stream with a CO-lean first gaseous stream; and
ii) stripping at least a portion of the carbon monoxide in the first furan stream into the first gaseous stream to produce a liquid second furan stream comprising less carbon monoxide than the first furan stream and a CO-enriched second gaseous stream.

DETAILED DESCRIPTION OF THE INVENTION

Figure 1:
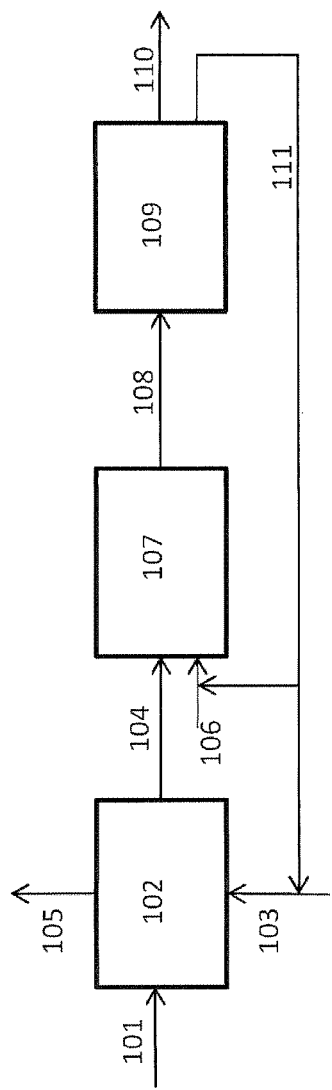
FIGS. 1, 2 and 3 are schematic diagrams of exemplary, but non-limiting, embodiments of the process described herein.

The present inventors have found that carbon monoxide may be separated from a liquid first furan stream comprising furan and carbon monoxide by contacting the first furan stream with a CO-lean first gaseous stream and stripping the carbon monoxide into said first gaseous stream. This first gaseous stream is preferably a gas stream that is already present in the furan production and/or upgrading process and can be selected in order to increase integration of gas streams throughout a process for the production of furan and its derivatives.

The first furan stream may be any liquid furan stream that comprises furan and carbon monoxide. Preferably, the first furan stream is provided by a reaction product stream from a reaction to produce furan, optionally after said reaction product stream undergoes some separation and/or purification steps.

The liquid first furan stream is contacted with first gaseous stream in such a manner that at least a portion of the carbon monoxide contained therein is stripped into the first gaseous stream. Any suitable method for gas/liquid contacting may be used. Exemplary methods for effecting said contact include, but are not limited to bubbling the first gaseous stream through the liquid first furan stream, spraying the liquid first furan stream into the first gaseous gas stream or flowing the first gaseous and liquid first furan streams over gas/liquid contacting devices. For instance, the gas/liquid contacting devices can consist of monolytic structures such as distillation trays, corrugated plates or grids, static mixers. However, it can also consist of structured or random beds of porous or non-porous structures such as beads, rings, cylinders, saddles and the likes.

The liquid first furan stream may be brought into contact with the first gaseous stream once or multiple times in order to strip the CO into the gaseous stream. In an alternative embodiment of the invention, the CO-lean first gaseous stream may comprise a number of separate gaseous streams that are contacted individually with the liquid first furan stream and then combined to provide the CO-enriched second gaseous stream.

At least a portion of the carbon monoxide present in the first furan stream is stripped into the CO-lean first gaseous stream to provide the CO-enriched second gaseous stream. Preferably at least 90 wt %, more preferably at least 95 wt %, even more preferably at least 99 wt %, even more preferably at least 99.5 wt %, most preferably at least 99.9 wt % of the carbon monoxide in the first furan stream is stripped into the CO-lean first gaseous stream to provide the CO-enriched second gaseous stream.

It will be apparent to the skilled person that the conditions of contacting the first gaseous stream and liquid first furan stream should be controlled in order to reduce the amount of furan that also is stripped along with the CO. Suitable conditions include increased pressure, reduced temperature and reduced volume flows of the first gaseous stream compared to that of the liquid first furan stream. The temperature is preferably no more than 150° C., more preferably no more than 100° C., even more preferably no more than 50° C. The pressure is preferably at least 0.2 MPa, more preferably at least 0.5 MPa, even more preferably at least 1 MPa, even more preferably at least 2 MPa, most preferably at least 5 MPa. The gas:liquid molar flow rate is preferably at most 10:1, more preferably at most 1:1, most preferably at most 0.1:1.

After absorbing at least a portion of the carbon monoxide in the first furan stream into the first gaseous stream, a liquid second furan stream comprising less carbon monoxide than the first furan stream and a CO-enriched second gaseous stream are produced.

The CO-lean first gaseous stream is preferably a gaseous stream present in the overall process system or in an associated process system. The CO-lean first gaseous stream preferably comprises one or more gases from the group consisting of hydrogen, nitrogen, carbon dioxide, steam and methane.

The term CO-lean as used herein refers to a stream preferably comprising no more than 10 vol % CO, more preferably no more than 1 vol % CO, even more preferably no more than 0.1 vol % CO, most preferably no more than 0.01 vol % CO.

The CO-enriched second gaseous stream will contain preferably at least two times, more preferably at least 5 times, even more preferably at least 10 times, most preferably at least 20 times the amount of CO present in the CO-lean first gaseous stream.

Preferably, the first gaseous stream comprises hydrogen. It may be a fresh gas stream comprising hydrogen. Preferably, it is a process gas stream from a process for producing furan and/or its derivatives or another process. Suitably said stream comprises at least 5 vol % hydrogen, preferably at least 20 vol % hydrogen, more preferably at least 50 vol % hydrogen.

Preferably, the first gaseous stream is a process stream from a process for producing furan and its derivatives. In a particularly preferred embodiment of the present invention, after steps i) and ii) the second furan stream is contacted with hydrogen in the presence of a hydrogenation catalyst to produce a hydrogenation reaction product stream comprising THF, n-butanol (NBA) and/or 1,4-BDO and hydrogen. This hydrogenation reaction product stream is then separated into a stream comprising THF, NBA and/or 1,4-BDO and a third gaseous stream comprising hydrogen. At least a portion of said third gaseous stream comprising hydrogen is then used as the first gaseous stream.

A further advantage of this embodiment of the invention is that as well as stripping carbon monoxide from the first furan stream into the first gaseous stream, any light ends in the third gaseous stream may be absorbed into the first furan stream and recycled into the reaction system.

Any suitable hydrogenation catalyst and conditions may be applied in this step of the process. Suitable catalysts include, but are not limited to group 8-11 metals supported on standard supports and unsupported 'skeletal/Raney' metals.

The hydrogenation reaction can proceed in the gas or the liquid phase. Suitable conditions for the production of mainly THF include the use of an inert or moderately polar solvent such as a hydrocarbon or oxygenate, a temperature in the range of from 50 to 250° C., a pressure of from 0.1 to 10 MPa and a $H_2$:furan molar ratio in the range of from 0.2:1 to 100:1, preferably in the range of from 0.2:1 to 10:1.

Suitable conditions for the production of a mixture of BDO and THF include co-feeding water as a gas or liquid at a water:furan molar ratio in the range of from 0.2:1 to 100:1. In this embodiment, further suitable conditions include the use of a solvent comprising water and/or hydrocarbon or oxygenates, preferably the reaction product (THF) or eventually by-products, a temperature in the range of from 100 to 350° C., preferably 150 to 250° C., a pressure of from 0.1 to 15 MPa and a $H_2$:furan molar ratio in the range of from 0.2:1 to 100:1, preferably in the range of from 2:1 to 10:1.

The hydrogenation reaction product stream will also comprise hydrogen and by-products from the hydrogenation reaction. A gas/liquid separation will be carried out at this point resulting in the third gaseous stream comprising hydrogen and also comprising low boiling by-products and a liquid stream comprising THF, NBA and/or 1,4-BDO and other higher boiling materials. There will, clearly, be slight cross-contamination of both of these streams. The resultant post-separation hydrogen-containing stream is at a slightly low pressure and would need to be moderately re-compressed for re-use in the hydrogenation reaction. Preferably, a bleed stream is removed from this stream in order to prevent build-up of low-boiling contaminants.

In a particularly preferred embodiment, this bleed stream is used as the first gaseous stream, either before or after it has been further de-pressurised.

The separated stream comprising THF, NBA and/or 1,4-BDO may be subjected to further processing and/or purification steps in order to produce desired products.

In the embodiment of the invention wherein the first furan stream is provided by a reaction product stream from a reaction to produce furan, preferably the furan present in the first furan stream is produced from furfural by a decarbonylation reaction in which the furfural is contacted with a decarbonylation catalyst in a decarbonylation reactor, preferably in the presence of hydrogen. The nature of the decarbonylation catalyst is not critical to the present invention and any catalyst suitable for the decarbonylation of furfural may be used.

Exemplary, but non-limiting, suitable decarbonylation catalysts include heterogeneous, supported catalysts.

These decarbonylation catalyst suitably contains a metal selected from the group consisting of iron, ruthenium, osmium, cobalt, rhodium, iridium, nickel, palladium, platinum and mixtures thereof.

Preferably, the metal in the decarbonylation catalyst is selected from the group consisting of Rh, Ir, Pd, Pt and mixtures thereof. More preferably, the metal in the decarbonylation catalyst is selected from the group consisting of Pd, Pt and a mixture of Pd and Pt. Even more preferably, the metal in the decarbonylation catalyst is Pd or Pt. Most preferably, the metal in the decarbonylation catalyst is Pd.

The total amount of the metal or metals selected from the group consisting of Fe, Ru, Os, Co, Rh, Ir, Ni, Pd, Pt and mixtures thereof may vary within wide ranges, and may be of from 0.01 to 20 wt %, 0.1 to 10 wt % or 0.5 to 5 wt % on the basis of the total weight of the catalyst. Preferably, the total amount of said metal or metals is at least 0.01 wt %, more preferably at least 0.05 wt %, more preferably at least 0.1 wt %, more preferably at least 0.3 wt %, more preferably at least 0.5 wt %, most preferably at least 0.7 wt %. Further, preferably, the total amount of said metal or metals is at most 20 wt %, more preferably at most 15 wt %, more preferably at most 10 wt %, more preferably at most 8 wt %, more preferably at most 5 wt %, most preferably at most 3 wt %.

Further to the above-mentioned metal or metals, the decarbonylation catalyst used in the process of the present invention may contain one or more additional metals, for example promoter metals. Suitable examples of such additional metals are alkali metals and/or alkaline earth metals. Preferably, the alkali metal is selected from the group consisting of sodium, potassium, rubidium and cesium. More preferably, the alkali metal is potassium.

The total amount of said additional metal or metals may vary within wide ranges, and may be of from 0.1 to 25 wt %, 0.5 to 15 wt % or 1 to 10 wt % on the basis of the total weight of the catalyst.

The nature of the support for the catalyst used in the process of the present invention is not essential. Said support may comprise carbon or one or more oxides selected from the group consisting of silica, alumina, barium sulfate, titanium dioxide, zirconium dioxide, magnesium silicate, diatomaceous earth and silica gel. In case the support comprises carbon, it may comprise, for example, activated carbon or carbon fibres.

During the decarbonylation step of the process of the present invention, the furfural may be contacted with the catalyst at a temperature in the range of from 100 to 450° C., preferably in the range of from 100 to 350° C., more preferably in the range of from 200 to 350° C., most preferably in the range of from 200 to 300° C., as mentioned above. The pressure during the furfural decarbonylation may be in the range of from 0.1 to 10 MPa, suitably 0.2 to 3 MPa, more suitably 0.3 to 1.5 MPa.

The decarbonylation step may be carried out in the liquid phase or gas phase. Preferably, it is carried out in the gas phase. If hydrogen is present, the molar ratio of hydrogen:furfural is preferably at least 0.1:1, more preferably at least 0.5:1.

As well as hydrogen, other gases may be provided to the decarbonylation step as a gas feed stream and said additional gas or gases may be selected from the group consisting of the noble gases, nitrogen, carbon monoxide, carbon dioxide, methane and steam. A suitable noble gas is argon. Preferably, if one or more additional gases are used, said gas feed stream comprises hydrogen and the additional gas or gases, for example nitrogen, in a volume ratio which is greater than 0.01:1 (hydrogen:additional gas or gases), more preferably greater than 0.1:1, more preferably greater than 1:1, more preferably greater than 5:1, more preferably greater than 10:1, more preferably greater than 50:1, more preferably greater than 100:1 and even more preferably greater than 1000:1.

Further, the hydrogen gas is suitably fed to the decarbonylation step at a rate of 0.01 to 100 Nl/g/h (normal liter per gram of catalyst per hour), preferably 0.1 to 10 Nl/g/h, more preferably 0.5 to 2 Nl/g/h. Further, the furfural may be fed at a rate of from 0.1 to 100 g/g/h (gram per gram of catalyst per hour), preferably 0.5 to 10 g/g/h.

The decarbonylation reaction product stream leaving the reactor in which the decarbonylation step occurs is preferably gaseous. This decarbonylation reaction product stream is optionally subjected to compression and/or cooling.

In one embodiment of the invention, compression and cooling occurs to such an extent that the furan is condensed to form the liquid first furan stream. In this embodiment, the decarbonylation reaction product stream is suitably compressed to at most 0.2 MPa, preferably at most 1 MPa, more preferably at most 2 MPa, even more preferably at most 5 MP, most preferably at most 10 MPa. Also in this embodiment, the decarbonylation reaction product stream is suitably cooled to a temperature no more than 150° C., preferably no more than 100° C., most preferably no more than 50° C.

In an alternative embodiment of the invention, the decarbonylation reaction product stream is subjected to a reduced amount or no compression and a reduced amount or no cooling. In this embodiment, if compression occurs, the decarbonylation reaction product stream is suitably compressed to at most 5 MPa, preferably at most 2 MPa, more preferably at most 1 MPa, even more preferably at most 0.5 MPa. Also in this embodiment, if cooling occurs, the decarbonylation reaction product stream is suitably cooled to a temperature no more than 150° C., preferably no more than 100° C., more preferably no more than 50° C., most preferably no more than 25° C. Such levels of cooling may be achieved using air or water cooling in most parts of the world.

After any compression and/or cooling and/or separation of condensed material, the decarbonylation reaction product stream may then be subjected to separation steps in order to provide the first furan stream of the process of the invention. In a particularly preferred embodiment of the invention, the decarbonylation reaction product stream is then contacted with a solvent stream, which is suitably a liquid solvent stream. Said solvent stream comprises one or more solvents in which furan is soluble. Suitable solvents include furfural, tetrahydrofurfural, tetrahydrofurfuryl alcohol, furfuryl alcohol, 1,4-BDO, ethers of 1,4-BDO and alcohols, n-butanol (NBA), dibutyl ether, ethylbutylether, oligomers of ethylene oxide and its ethers, γ-butyrolactone (GBL), THF, 2,2-bifuran, 2,2-methylene bifuran and other hydrogenated and/or alkylated and or hydroxymethylated bifurans, other oxygenates, aromatic solvents, oxygenated aromatic solvents and hydrocarbons, such as alkanes. Preferably, the solvent is selected from one or more materials involved in the process of the invention or in a subsequent conversion step of the furan. More preferably, the solvent is selected from furfural, 1,4-BDO, NBA, THF, 2,2-bifuran, 2,2-methylene bifuran and other hydrogenated and/or alkylated and or hydroxymethylated bifurans.

The solvent stream is contacted with the decarbonylation reaction product stream in any suitable method for gas/liquid contacting. The contacting can be performed in co-, counter- or cross-flow. Exemplary suitable methods for effecting said contact include, but are not limited to, bubbling the gas stream through the liquid solvent stream, spraying the liquid solvent stream into a the gas stream or flowing the gas and liquid streams over gas/liquid contacting devices. For instance, the gas/liquid contacting devices can consist of monolytic structures such as distillation trays, corrugated plates or grids, static mixers. However, it can also consist of structured or random beds of porous or non-porous structures such as beads, rings, cylinders, saddles and the likes.

The solvent stream may be brought into contact with the decarbonylation reaction product stream once or multiple times in order to absorb the furan into the solvent stream. In an alternative embodiment of the invention, the solvent stream may comprise a number of separate solvent streams that are contacted individually with the decarbonylation reaction product stream and then combined.

Suitably the solvent stream contains solvent such that the molar ratio of solvent:furan is at least 0.1:1, preferably at least 0.2:1, more preferably at least 0.5:1. Further, the solvent stream suitably contains solvent such that the molar ratio of solvent:furan is at most 50:1, preferably at most 20:1, more preferably at most 20:1.

At least a portion of the furan in the decarbonylation reaction product stream after any optional compression and/or cooling is absorbed into the solvent stream to provide a furan-containing solvent stream. Preferably at least 90 wt %, more preferably at least 95 wt %, even more preferably at least 99 wt %, even more preferably at least 99.5 wt %, most preferably at least 99.9 wt % of the furan in the decarbonylation reaction product stream after any optional compression and/or cooling is absorbed into the solvent stream to produce a furan-containing solvent stream.

After absorption of the furan into the solvent stream, the remaining gaseous stream comprises hydrogen and carbon monoxide. It is likely that this stream will also contain some furan and solvent. This stream may be recycled, partially recycled, used as fuel or supplied to a different reaction, e.g. a water-gas shift reaction.

Preferably, in this embodiment of the invention, the furan is separated from the furan-containing solvent stream by distillation to provide the first furan stream. This may be achieved without substantial loss of the furan. Alternatively, it may be suitable to use the furan-containing solvent stream as the first furan stream without further separation. In this embodiment, it is preferred that, the solvent used in the solvent stream is a material which is compatible with, present or formed in a later transformation of the furan.

If the furan-containing solvent stream is subjected to a distillation step in which the furan is separated from the solvent to form the first furan stream, the distillation may be carried out under any suitable conditions, depending on the solvent used. In a preferred embodiment of the invention, the solvent used has a higher boiling point than furan and the furan is, therefore, distilled off the solvent as top product.

The solvent may then be recycled for reuse in the solvent stream. In a preferred embodiment of the invention, the solvent used is furfural. In this embodiment of the invention, the furfural may be recycled for re-use in the solvent stream. However, in a particularly preferred embodiment of the invention, furfural is used as the solvent in the solvent stream and after at least a portion of the furan has been separated from the furan-containing solvent stream, at least a portion of the remaining furfural, containing any residual furan, is then passed to the decarbonylation reactor as a reaction feedstock.

DETAILED DESCRIPTION OF THE DRAWINGS

The invention will now be further illustrated with reference to the non-limiting embodiments shown in the drawings. In the drawings, the first numeral of each reference number refers to the Figure number, e.g. 1XX for FIG. 1 and 2XX for FIG. 2. The remaining figures relate to the individual features within the Figures. The same number is used to refer to the same feature in each Figure. Therefore, 107 refers to the same feature in FIG. 1 as 207 refers to in FIG. 2.

In a preferred, but non-limiting, embodiment of the invention illustrated in FIG. 1, a first liquid furan stream 101 is contacted with a CO-lean first gaseous stream 103 in a vessel 102. This results in a second gaseous stream 105 containing at least a portion of the carbon monoxide present in the first liquid furan stream 101 and a second liquid furan stream 104, which contains less carbon monoxide than the first liquid furan stream 101.

The second liquid furan stream 104 is contacted with a hydrogen gas stream 106 in a hydrogenation reactor 107 to produce a hydrogenation reaction product stream 108. Said hydrogenation reaction product stream 108 will contain THF and/or 1,4-BDO and hydrogen. This is then separated in a vessel 109 to produce a THF and/or 1,4-BDO-containing stream 110 and a third gaseous stream 111, a portion of which can be used as the first gaseous stream 103. The remainder of the third gaseous stream 111 can be re-used as at least a part of the hydrogen stream 106.

Figure 2:
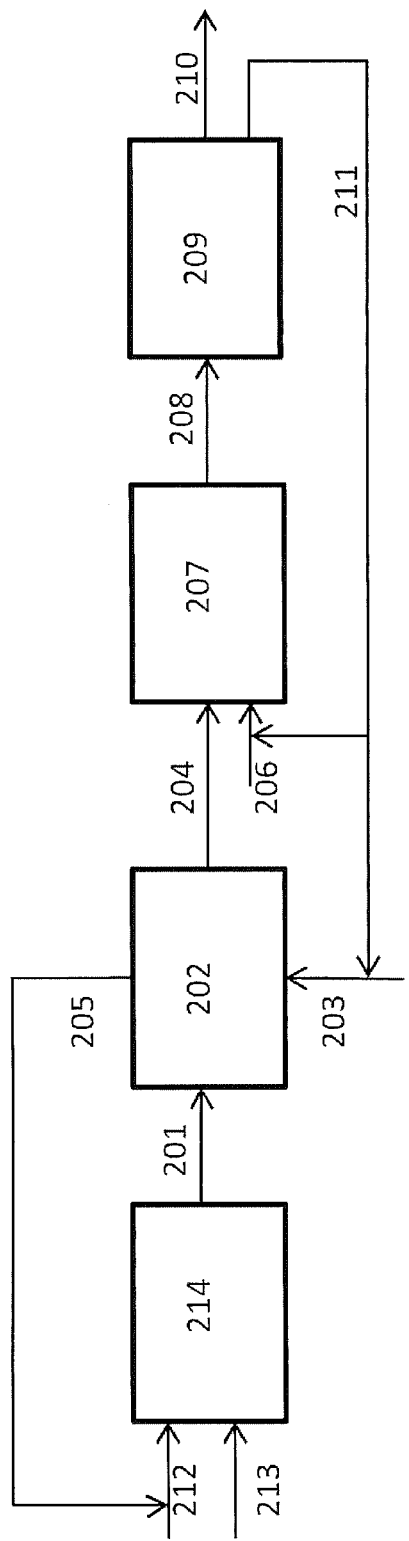

In a particularly preferred, but non-limiting embodiment of the invention illustrated in FIG. 2, the first liquid furan stream 201 is produced by a reaction of furfural 213 and a source of hydrogen 212 in the presence of a decarbonylation catalyst in a decarbonylation reactor 214 and, optionally, further processing steps of the resultant decarbonylation reaction product stream, such as cooling and/or compression. The second gaseous stream 205 is used as at least a portion of the source of hydrogen 212.

Figure 3:
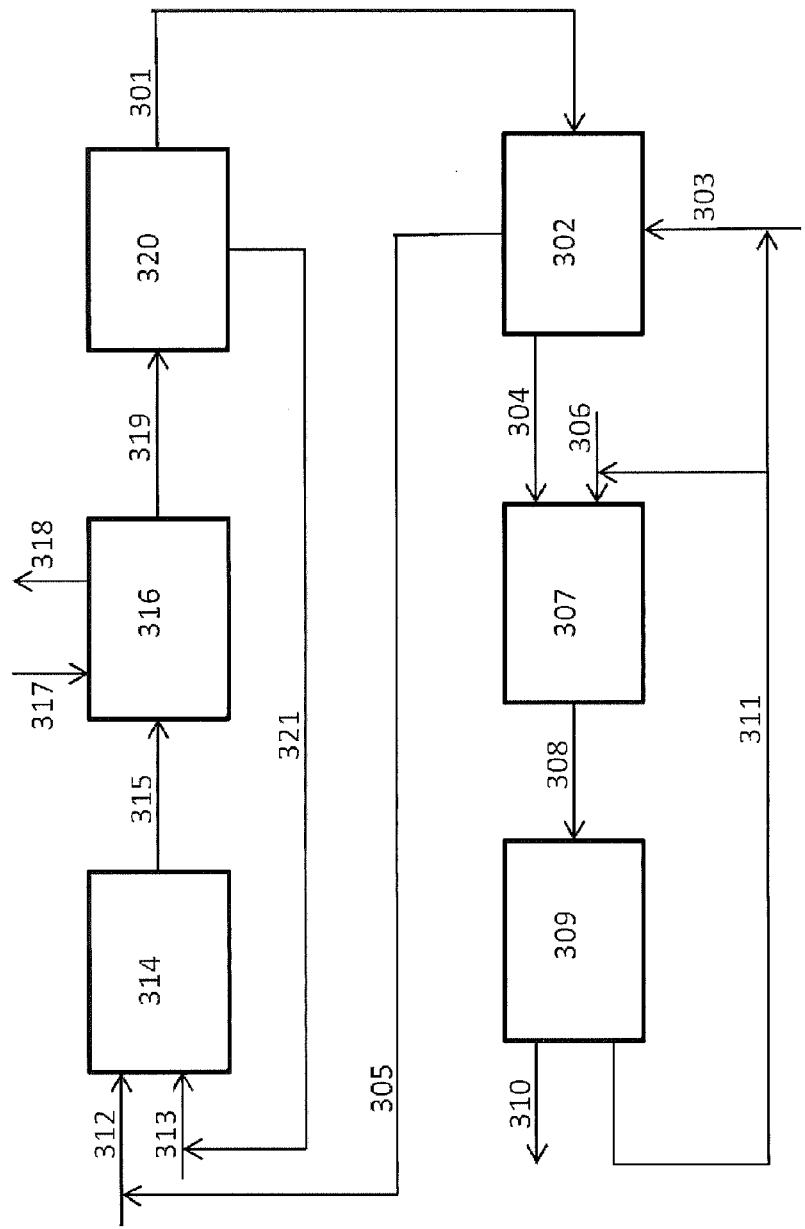

In a further particularly preferred, but non-limiting, embodiment of the invention illustrated in FIG. 3, the decarbonylation reaction product stream 315 is contacted with a solvent stream 317 comprising furfural in a vessel 316 to provide a furan-containing solvent stream 319. Hydrogen and carbon monoxide are removed as a gaseous stream 318. The furan-containing solvent stream 319 is subjected to distillation in a distillation column 320, providing the first furan stream 301 and a solvent stream 321 for recycle to the decarbonylation reactor 314 as the source of furfural.

The invention will now be illustrated by the following, non-limiting examples.

EXAMPLES

Example 1

A process line-up was developed in ASPEN, using a fit for purpose thermodynamic data deck. The liquid product stream from a decarbonylation reactor and initial furan isolation consisted of 99.88 mol % furan, 0.0054 mol % $H_2$ and 0.12 mol % CO at 400 kPa and 50° C., in phase equilibrium with a partial pressure of 200 kPa in CO. This first furan stream was contacted at 400 kPa and 50° C. with a gaseous stream composed of 6.1 mol % furan, 93.8 mol % $H_2$ and 0.093 mol % CO, resulting in a second liquid furan stream consisting of 98.7 mol % furan, 1.2 mol % $H_2$ and 0.0192 mol % CO and a gaseous stream consisting of 6.6 mol % furan, 92.7 mol % $H_2$ and 0.69 mol % CO.

The second liquid furan stream was contacted at 4000 kPa and 50° C. with a gaseous stream composed of 100 mol % $H_2$, resulting in a third liquid furan stream consisting of 98.8 mol % furan, 1.2 mol % $H_2$ and 0.0026 mol % CO and a gaseous stream consisting of 6.1 mol % furan, 93.8 mol % $H_2$ and 0.093 mol % CO.

Example 2

In a two-stage stripper system identical to Example 1, CO is removed from the furan stream using a purge stream obtained from the subsequent hydrogenation reactor, in line with FIG. 1. The liquid product stream from an decarbonylation reactor and after initial furan isolation consisted 99.88 mol % furan, 0.0054 mol % $H_2$ and 0.12 mol % CO at 400 kPa and 50° C., in phase equilibrium with a partial pressure of 200 kPa in CO. This first liquid furan stream was contacted at 400 kPa and 50° C. with a gaseous stream composed of 6.2 mol % furan, 93.7 mol % $H_2$ and 0.082 mol % CO, resulting in a second liquid furan stream consisting of 98.7 mol % furan, 1.3 mol % $H_2$ and 0.017 mol % CO and a gaseous stream consisting of 6.6 mol % furan, 92.7 mol % $H_2$ and 0.61 mol % CO.

The second liquid furan stream was contacted at 4000 kPa and 50° C. with a gaseous stream composed of 1.9 mol % furan, 97.3 mol % $H_2$ and 0.01 mol % CO, resulting in a third furan stream consisting of 98.6 mol % furan, 1.2 mol % $H_2$ and 0.0023 mol % CO and a gaseous stream consisting of 6.2 mol % furan, 93.7 mol % $H_2$ and 0.082 mol % CO.

That which is claimed is:

1. A process for the treatment of a liquid first furan stream comprising furan and carbon monoxide, said process comprising the steps of:
   i) contacting said first furan stream with a CO-lean first gaseous stream; and
   ii) stripping at least a portion of the carbon monoxide in the first furan stream into the first gaseous stream to produce a liquid second furan stream comprising less carbon monoxide than the first furan stream and a CO-enriched second gaseous stream.

2. A process according to claim 1, wherein the CO-lean first gaseous stream comprises one or more gases from the group consisting of hydrogen, nitrogen, carbon dioxide, steam and methane.

3. A process according to claim 2, wherein the CO-lean first gaseous stream comprises hydrogen.

4. A process according to claim 1, wherein the CO-lean first gaseous stream comprises no more than 10 vol % CO.

5. A process according to claim 1, wherein the process further comprises the steps of:
   i) contacting a second furan stream with hydrogen in the presence of a hydrogenation catalyst to produce a hydrogenation reaction product stream comprising THF, n-butyl alcohol (NBA) and/or 1,4-BDO and hydrogen;
   ii) separating the hydrogenation reaction product stream into a stream comprising THF, NBA and/or 1,4-BDO and a third gaseous stream comprising hydrogen; and
   iii) using at least a portion of said third gaseous stream comprising hydrogen as the first CO-lean gaseous stream.

6. A process according to claim 1, wherein the hydrogenation catalyst comprises one or more metals selected from groups 8 to 11 of the periodic table.

7. A process according to claim 1, wherein the liquid first furan stream is produced in a process comprising the steps of contacting furfural with a decarbonylation catalyst to produce a decarbonylation reaction product stream; and further processing the decarbonylation reaction product stream in order to provide the liquid first furan stream.

8. A process according to claim 7, wherein the furfural is contacted with the decarbonylation catalyst in the presence of hydrogen.

9. A process according to claim 8, wherein the CO-enriched second gas stream is subsequently used to provide the source of said hydrogen.

10. A process according to claim 7, wherein, the decarbonylation reaction product stream is subjected to compression and/or cooling in order to provide the liquid first furan stream.

11. A process according to claim 7, wherein, optionally after cooling and/or compression, the decarbonylation reaction product stream is contacted with a solvent stream and at least a portion of the furan present is absorbed into the solvent stream to provide a furan-containing solvent stream.

12. A process according to claim 11, wherein the furan-containing solvent stream is used as the first furan stream.

13. A process according to claim 11, wherein the first furan stream is produced from the furan-containing solvent stream by distillation.

* * * * *